United States Patent
Walicki

(10) Patent No.: US 9,841,382 B2
(45) Date of Patent: *Dec. 12, 2017

(54) METHODS AND SYSTEMS FOR ANALYZING A LIQUID MEDIUM

(71) Applicant: Ecolab USA Inc., Naperville, IL (US)

(72) Inventor: Robert S. Walicki, Oak Park, IL (US)

(73) Assignee: Ecolab USA Inc., Naperville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/142,605

(22) Filed: Apr. 29, 2016

(65) Prior Publication Data

US 2016/0238539 A1 Aug. 18, 2016

Related U.S. Application Data

(63) Continuation of application No. 13/789,935, filed on Mar. 8, 2013, now Pat. No. 9,329,159.

(51) Int. Cl.
*G01N 21/78* (2006.01)
*G01N 31/22* (2006.01)
(Continued)

(52) U.S. Cl.
CPC ......... *G01N 21/78* (2013.01); *G01N 21/8483* (2013.01); *G01N 31/22* (2013.01);
(Continued)

(58) Field of Classification Search
CPC ..... G01N 2021/752; G01N 2021/7759; G01N 21/78; G01N 21/8483; G01N 31/22; G01N 33/18
(Continued)

(56) References Cited

U.S. PATENT DOCUMENTS 5,094,957 A * 3/1992 Willingham ........... G01N 21/29
436/164
5,126,247 A * 6/1992 Palmer ..................... C12Q 1/26
435/174

(Continued)

FOREIGN PATENT DOCUMENTS

EP         1970698 A2    9/2008
WO   WO 2011/008581 A2   1/2011
(Continued)

OTHER PUBLICATIONS

Kim et al, Electrochemical detection of arsenic via a microfluidic sensor and mobile interface towards affordable, rapid, and point-of-use water monitoring, 2013.*
(Continued)

*Primary Examiner* — Shan Elahi
(74) *Attorney, Agent, or Firm* — Leydig, Voit & Mayer, Ltd.

(57) ABSTRACT

Methods and systems for colorimetrically analyzing a liquid medium by analyzing chemical test strip images are provided. The liquid medium can be industrial water in an industrial water system. Image analyzing software carries out the analysis. The results of the analysis can be used to diagnosing a chemical treatment regimen of the industrial water system. A chemical test strip holder can be used to enhance reliability and repeatability of the imaging process and/or subsequent analysis.

20 Claims, 3 Drawing Sheets

(51) Int. Cl.
*G01N 21/84* (2006.01)
*G01N 21/75* (2006.01)
*G01N 21/77* (2006.01)
*G01N 33/18* (2006.01)

(52) U.S. Cl.
CPC ....... *G01N 33/18* (2013.01); *G01N 2021/752* (2013.01); *G01N 2021/7759* (2013.01)

(58) Field of Classification Search
USPC ........................................................ 348/135
See application file for complete search history.

(56) References Cited

U.S. PATENT DOCUMENTS

| | | | | |
|---|---|---|---|---|
| 5,171,451 | A * | 12/1992 | Khambatta | C02F 1/50 210/701 |
| 5,210,207 | A * | 5/1993 | Mokhtarzadeh | C07C 67/10 548/239 |
| 5,258,314 | A | 11/1993 | Skerratt | |
| 5,603,840 | A * | 2/1997 | Strittmatter | C02F 1/766 162/161 |
| 5,792,369 | A * | 8/1998 | Johnson | C02F 1/32 204/293 |
| 6,156,229 | A * | 12/2000 | Yang | A61L 2/18 252/186.1 |
| 6,265,477 | B1 | 7/2001 | Hurlock | |
| 6,295,506 | B1 * | 9/2001 | Heinonen | A61B 5/14532 600/301 |
| 6,696,240 | B1 * | 2/2004 | Kloepfer | G01N 33/558 422/412 |
| 8,935,007 | B2 * | 1/2015 | Kloepfer | G01N 21/78 340/539.12 |
| 9,255,526 | B2 * | 2/2016 | Hatcher, Jr. | F02C 7/00 |
| 2002/0105346 | A1 * | 8/2002 | Banks | G01N 17/02 324/700 |
| 2002/0173704 | A1 * | 11/2002 | Schulze | A61B 5/0002 600/300 |
| 2002/0186882 | A1 | 12/2002 | Cotman et al. | |
| 2003/0215936 | A1 | 11/2003 | Kallioniemi et al. | |
| 2004/0085443 | A1 | 5/2004 | Kallioniemi et al. | |
| 2005/0134853 | A1 | 6/2005 | Ingleson et al. | |
| 2005/0201898 | A1 | 9/2005 | Borich et al. | |
| 2006/0062688 | A1 * | 3/2006 | Lawrence | G01N 21/78 422/400 |
| 2006/0222567 | A1 | 10/2006 | Kloepfer et al. | |
| 2007/0077178 | A1 * | 4/2007 | Wagner | G01N 21/51 422/82.08 |
| 2007/0183930 | A1 | 8/2007 | Roman | |
| 2008/0274495 | A1 * | 11/2008 | Jumonville | A61B 10/007 435/30 |
| 2009/0247857 | A1 * | 10/2009 | Harper | A61B 5/14532 600/365 |
| 2010/0072371 | A1 * | 3/2010 | Wagner | G01N 21/51 250/343 |
| 2010/0239137 | A1 * | 9/2010 | Pugia | G01N 21/274 382/128 |
| 2010/0254581 | A1 | 10/2010 | Neeser et al. | |
| 2012/0142113 | A1 * | 6/2012 | Banks | G01N 21/643 436/43 |
| 2012/0165626 | A1 * | 6/2012 | Irina | A61B 5/14517 600/316 |
| 2012/0273112 | A1 | 11/2012 | Dagenbach et al. | |

FOREIGN PATENT DOCUMENTS

| | | |
|---|---|---|
| WO | WO 2012/012382 A1 | 1/2012 |
| WO | WO 2012/131386 A1 | 10/2012 |
| WO | WO 2013/010178 A1 | 1/2013 |

OTHER PUBLICATIONS

European Patent Office, Extended European Search Report in European Patent Application No. 14759928.6, Oct. 24, 2016, 10 pp.

* cited by examiner

METHODS AND SYSTEMS FOR ANALYZING A LIQUID MEDIUM

CROSS-REFERENCE TO RELATED APPLICATIONS

This application is a continuation of U.S. patent application Ser. No. 13/789,935, filed Mar. 8, 2013, the disclosure of which is incorporated by reference herein in its entirety for all purposes.

FIELD

The disclosure is directed toward analyzing chemical species in a liquid medium using a chemical test strip and an imaging device.

BACKGROUND

Advances in digital imaging and communication have grown considerably over the last fifteen years. The disclosure at hand is directed generally toward digital imaging technology, and is particularly suitable for hand held devices such as a mobile phone that incorporates a camera. It was nearly unheard of to have a camera on a mobile phone in 1998. Such technology was expensive and the resolution at that time was poor in comparison to that found on more modern devices. With the advances in imaging devices and microelectronics, it is now commonplace for a person to have a mobile phone that incorporates a reasonably high resolution camera. While modern mobile phones are regularly used to take and share pictures of families and friends, such devices may be used for other purposes. In accordance with the general inventive concepts, one such purpose is to capture and perhaps analyze a digital image for scientific or industrial purposes.

SUMMARY

In a first exemplary embodiment, the present disclosure is directed toward a method of colorimetrically determining a concentration of at least one chemical species in a liquid medium. The method comprises providing a chemical test strip comprising a reactive zone, an imaging device, and image analyzing software. The reactive zone of the chemical test strip is exposed to at least a portion of the liquid medium thereby creating a post-exposure reactive zone. The post-exposure reactive zone is then imaged using the imaging device thereby creating a digital image of the post-exposure reactive zone. Optionally, the digital image may be cropped thereby isolating a portion of the image for analysis. At least the portion of the digital image of the post-exposure reactive zone is analyzed using the image analyzing software to determine the concentration of the at least one chemical species. The image analyzing software analyzes at least one colorimetric parameter of the digital image to determine the concentration of the at least one chemical species within the liquid medium. Optionally, the determined concentration of the at least one chemical species of the liquid medium is output, and action may be optionally taken to implement chemical treatment based on the determined concentration.

In a second exemplary embodiment, the present disclosure is directed toward a corresponding system for colorimetrically determining a concentration of at least one chemical species in a liquid medium. The system comprises a chemical test strip, an imaging device, and image analyzing software. The chemical test strip has a reactive zone suitable for exposure to the liquid medium. The imaging device is capable of creating a digital image of the reactive zone of the chemical test strip after the reactive zone has been exposed to the liquid medium. The image analyzing software is capable of analyzing at least one colorimetric parameter of the digital image of the reactive zone. The image analyzing software is also capable of determining the concentration of the at least one chemical species in the liquid medium based on the analysis of the at least one colorimetric parameter.

In a third exemplary embodiment, the present disclosure is directed toward an apparatus for holding a chemical test strip having at least one reactive zone. The apparatus comprises a chemical test strip holder and a battery-powered light emitting diode. The chemical test strip holder has an opening that allows a chemical test strip to be displayed at a given distance within an imaging chamber created by the chemical test strip holder. The battery-powered light emitting diode is located within the imaging chamber and behind the opening of the chemical test strip holder. The battery-powered light emitting diode is capable of shining light from behind the at least one reactive zone.

BRIEF DESCRIPTION OF THE DRAWINGS

Various aspects and advantages of the present disclosure will become more readily apparent to those of ordinary skill in the relevant art after reviewing the following detailed description and accompanying drawings, wherein:

FIG. 4b shows a top cutaway view of the inside (i.e., top wall removed) of the exemplary embodiment of the test strip stabilizer illustrated in FIGS. 2, 3, and 4a.

DETAILED DESCRIPTION

Figure 1:
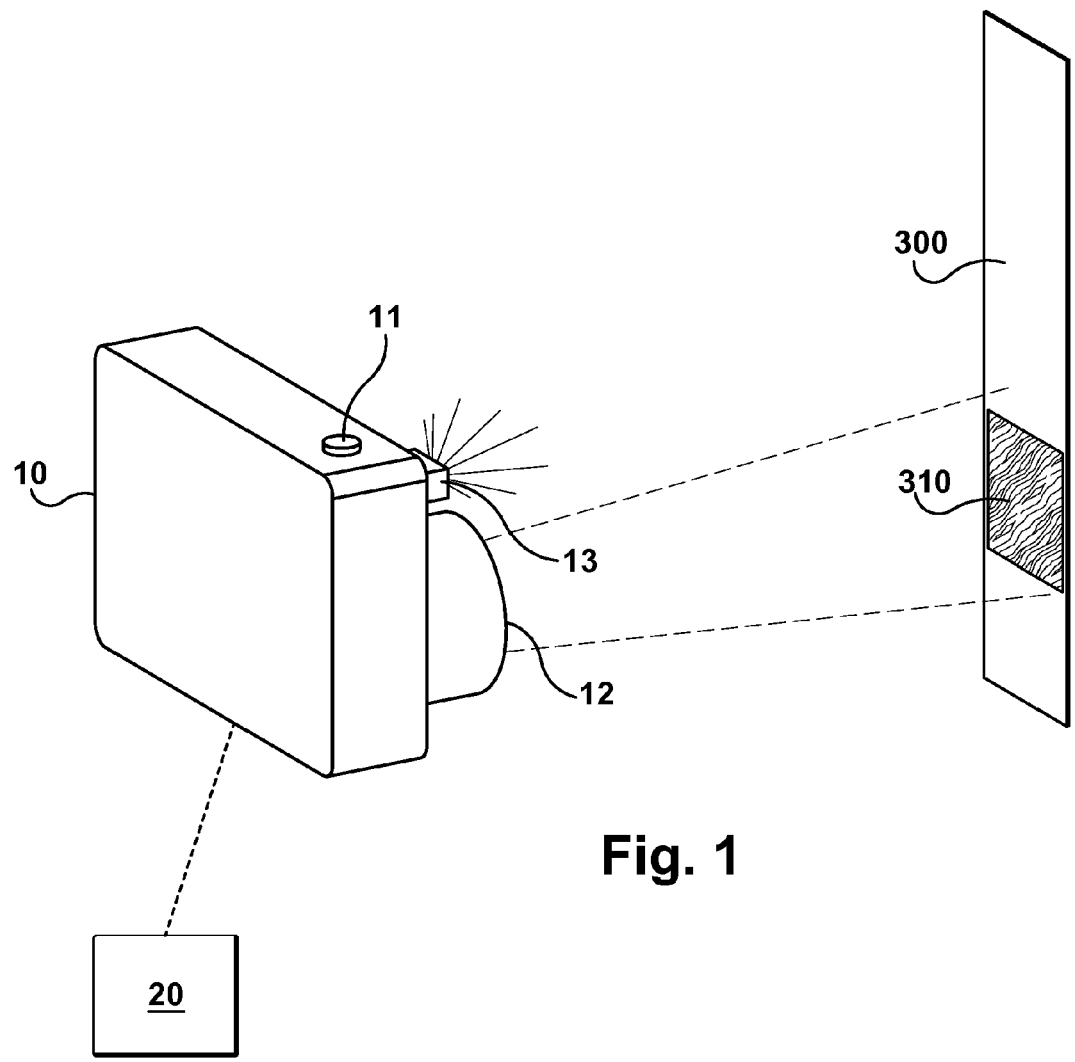
FIG. 1 illustrates an exemplary embodiment of an imaging device imaging a reactive zone of a chemical test strip.

While embodiments encompassing the general inventive concepts may take various forms, there is shown in the drawings and will hereinafter be described various embodiments with the understanding that the present disclosure is to be considered merely an exemplification and is not intended to be limited to the specific embodiments.

As it pertains to the present disclosure, "logic" (synonomous with "circuit") includes, but is not limited to, hardware, firmware, software, and/or combinations of each to perform a function(s) or an action(s). For example, based on a desired application or needs, logic may include a software controlled microprocessor, discreet logic such as an application specific integrated circuit ("ASIC"), or other programmed logic device. In some instances, logic could also be fully embodied as software.

As it pertains to the present disclosure, "software" or "computer program" refer to one or more computer readable and/or executable instructions that cause a computer or other electronic device to perform functions, actions, and/or behave in a desired manner. The instructions may be embodied in various forms such as routines, algorithms, modules, or programs including separate applications or code from dynamically linked libraries. Software may also be implemented in various forms such as a stand-alone program, a function call, a servlet, an applet, instructions stored in a memory, part of an operating system, or other type of executable instructions. It will be appreciated by one of ordinary skill in the art that the form of software is dependent on, for example, requirements of a desired application, the environment executing the program, and/or the desires of a designer/programmer or the like.

As it pertains to this disclosure, "computer" or "processing unit" includes, but is not limited to, any programmed or programmable electronic device that can store, retrieve, and process data.

As it pertains to the present disclosure, "industrial water" is water that is used in some capacity in an industrial process. Non-limiting examples of industrial water include water used in a primary industrial process (i.e., one that makes an intermediate or product) or a secondary industrial process such as a heating or cooling system, which includes but is not limited to water that is added to, passed through, circulated in, or removed from an aqueous cooling system, a boiler system, a hot water system, and the like.

As it pertains to this disclosure, "change color" refers to the action of becoming a different color or a different shade of the same color. By changing color, a post-exposure reactive zone can provide an indication of the presence and possibly concentration of a chemical species within a liquid medium. For an exposure zone, a change in color indicates that the test strip has been exposed to a liquid medium.

In a first exemplary embodiment, the present disclosure is directed toward a method of colorimetrically determining a concentration of at least one chemical species in a liquid medium. The method comprises providing a chemical test strip comprising a reactive zone, an imaging device, and image analyzing software. The reactive zone of the chemical test strip is exposed to at least a portion of the liquid medium thereby creating a post-exposure reactive zone. The post-exposure reactive zone is then imaged using the imaging device thereby creating a digital image of the post-exposure reactive zone. Optionally, the digital image may be cropped thereby isolating a portion of the image for analysis. At least the portion of the digital image of the post-exposure reactive zone is analyzed using the image analyzing software to determine the concentration of the at least one chemical species. The image analyzing software analyzes at least one colorimetric parameter of the digital image to determine the concentration of the at least one chemical species within the liquid medium. Optionally, the determined concentration of the at least one chemical species of the liquid medium is output, and action may be optionally taken to implement chemical treatment based on the determined concentration.

In a second exemplary embodiment, the present disclosure is directed toward a corresponding system for colorimetrically determining a concentration of at least one chemical species in a liquid medium. The system comprises a chemical test strip, an imaging device, and image analyzing software. The chemical test strip has a reactive zone suitable for exposure to the liquid medium. The imaging device is capable of creating a digital image of the reactive zone of the chemical test strip after the reactive zone has been exposed to the liquid medium. The image analyzing software is capable of analyzing at least one colorimetric parameter of the digital image of the reactive zone. The image analyzing software is also capable of determining the concentration of the at least one chemical species in the liquid medium based on the analysis of the at least one colorimetric parameter.

In a third exemplary embodiment, the present disclosure is directed toward an apparatus for holding a chemical test strip having at least one reactive zone. The apparatus comprises a chemical test strip holder and a battery-powered light emitting diode. The chemical test strip holder has an opening that allows a chemical test strip to be displayed at a given distance within an imaging chamber created by the chemical test strip holder. The battery-powered light emitting diode is located within the imaging chamber and behind the opening of the chemical test strip holder. The battery-powered light emitting diode is capable of shining light from behind the at least one reactive zone.

In certain exemplary embodiments of the disclosed methods and systems, a concentration of a dissolved chemical species in a liquid medium is determined via digital imaging analysis. In certain other exemplary embodiments, a plan of action to maintain efficient operation of an industrial water system is automatically recommended based on the digital imaging analysis. In certain exemplary embodiments, the recommended plan of action is to continue with the same chemical treatment regimen. In the embodiments that recommend a plan of action, determining the plan of action may requires only one additional step beyond determining the chemical species concentration. In other words, in some exemplary embodiments, the plan of action may be determined based solely on the determined presence or concentration of a dissolved chemical species in industrial water.

The aforementioned chemical test strips are commonly used to determine the concentration of one or more chemical species within any of a variety of liquid media. As it pertains to the exemplary embodiments disclosed herein, "liquid medium" (plural: "liquid media") refers to any liquid-comprising substance (e.g., includes slurries) that may contain a soluble or miscible species within the liquid portion of the substance. In order to determine the concentration of the one or more chemical species, a reactive zone on the chemical test strip must be exposed to at least a portion of the liquid medium. In certain exemplary embodiments the liquid medium is water, which may be industrial water.

In certain exemplary embodiments, the reactive zone of the chemical test strip is exposed to (e.g., dipped into) a sample of the liquid medium that has been removed from an industrial process. In certain exemplary embodiments, the reactive zone of the chemical test strip is exposed to a liquid medium that is active within an industrial process.

Certain exemplary embodiments of the chemical test strip have at least one reactive zone that changes color upon exposure to a particular chemical species. Certain other exemplary embodiments of the chemical test strip have at least one reactive zone that changes shade of a color (i.e., color intensity). In certain exemplary embodiments, the chemical test strip may test for the presence or concentration of a soluble impurity present in the liquid medium. In certain exemplary embodiments, the chemical test strip may test for the presence or concentration of a soluble treatment chemical in the liquid medium. Non-limiting examples of chemical test strips include those that are able to test for presence or concentration of dissolved calcium, acidity (i.e., pH), concentration of total hardness, chloride concentration, total residual chloride, free chloride residual, ortho-phosphate, m-alkalinity, and p-alkalinity. In certain exemplary embodiments, the chemical test strip are able to test for the presence and/or concentration of one or more treatment chemicals. Non-limiting examples of such test strips include those that test for the presence and/or concentration of a corrosion inhibitor, a dispersant polymer, a biocide, and combinations thereof.

Non-limiting examples of corrosion inhibitors include aromatic azoles (e.g., triazoles and aromatic (thio)(tri)

azoles). Non-limiting examples of aromatic azoles include mercaptobenzothiazole ("MBT"), benzotriazole ("BT"), butylbenzotriazole ("BBT"), tolytriazole ("TT"), naphthotriazole ("NTA") and related compounds.

As it pertains to this disclosure, "dispersion polymer" means a water-soluble polymer dispersed in an aqueous continuous phase containing one or more inorganic salts. In the process of dispersion polymerization, the monomer and the initiator are both soluble in a polymerization medium, but the medium is a poor solvent for the resulting polymer. Accordingly, the reaction mixture is homogeneous at the onset, and polymerization is initiated in a homogeneous solution. Depending on the solvency of the medium for the resulting oligomers or macroradicals and macromolecules, phase separation occurs at an early stage, leading to nucleation and the formation of primary particles called "precursors." The precursors are colloidally stabilized by adsorption of stabilizers. The particles are believed to be swollen by the polymerization medium and/or the monomer, leading to the formation of spherical particles having a size in the region of about 0.1-10 microns. Non-limiting examples of dispersant polymers include those listed in and/or defined by U.S. Pat. No. 6,265,477 to Hurlock, the disclosure of which is herein incorporated in its entirety.

Non-limiting examples of biocides include oxidizing biocides, non-oxidizing biocides, or physical biocides. Physical biocides may include, for example, steam sterilization or ultraviolet radiation. Oxidizing biocides include, but are not limited to, stabilized oxidants and halogenated oxidants, which may include chlorine bleach; chlorine; bromine; iodine; materials capable of releasing chlorine, bromine, and/or iodine; inorganic peroxides; organic peroxides; chlorine dioxide; ethylene oxide; ozone; chloramines compounds; precursors thereof, and combinations thereof. Non-oxidizing biocides include, but are not limited to, quaternary ammonium compounds; glutaraldehyde; isothiazolin; 2,2-dibromo-3-nitrilopropionamide; 2-bromo-2-nitropropane-1, 3-diol; 1-bromo-1-(bromomethyl)-1,3-propanedicarbonitrile; tetrachloroisophthalonitrile; alkyldimethylbenzylammonium chloride; dimethyl dialkyl ammonium chloride; didecyl dimethyl ammonium chloride; poly(oxyethylene(dimethyliminio)ethylene(dimethyliminio)ethylene dichloride; methylene bisthiocyanate; 2-decylthioethanamine; tetrakishydroxymethyl phosphonium sulfate; dithiocarbamate; cyanodithioimidocarbonate; 2-methyl-5-nitroimidazole-1-ethanol; 2-(2-bromo-2-nitroethenyl)furan; beta-bromo-beta-nitrostyrene; beta-nitrostyrene; beta-nitrovinyl furan; 2-bromo-2-bromomethyl glutaronitrile, bis(trichloromethyl) sulfone; S-(2-hydroxypropyl)thiomethanesulfonate; tetrahydro-3,5-dimethyl-2H-1,3,5-hydrazine-2-thione; 2-(thiocyanomethylthio)benzothiazole; 2-bromo-4'-hydroxyacetophenone; 1,4-bis (bromoacetoxy)-2-butene; bis(tributyltin)oxide; 2-(tert-butylamino)-4-chloro-6-(ethylamino)-s-triazine; dodecylguanidine acetate; dodecylguanidine hydrochloride; coco alkyldimethylamine oxide; n-coco alkyltrimethylenediamine; tetra-alkyl phosphonium chloride; 7-oxabicyclo[2.2.1]heptane-2,3-dicarboxylic acid; 4,5-dichloro-2-n-octyl-4-isothiazoline-3-one; 5-chloro-2-methyl-4-isothiazolin-3-one; 2-methyl-4-isothiazolin-3-one; precursors thereof and combinations thereof.

Because a chemical test strip may be used to test for a chemical species that is not present in the tested liquid medium, it is often important or otherwise beneficial to have a definitive indication that the chemical test strip has actually been exposed to the liquid medium at issue. For such situations, the chemical test strip may include an "exposure zone," which is a zone that changes color as previously defined when exposed to a known liquid medium, typically water. Certain exemplary embodiments of the chemical test strips may employ an exposure zone to indicate whether the chemical test strip has been exposed to a particular liquid medium.

Certain exemplary embodiments of the chemical test strips include a "standard zone," which is a zone on the chemical test strip that is the same color as a corresponding unexposed reactive zone on the chemical test strip. The standard zone gives a reference point for the color change of the exposed reactive zone because the standard zone does not change color upon exposure to the particular chemical species.

In certain exemplary embodiments of the chemical test strip, the presence or concentration of the at least one chemical species is determined via a plurality of post-exposure reactive zones on the chemical test strip. In certain exemplary embodiments, the plurality of post-exposure reactive zones provides information related to the concentration of an individual species within the liquid medium. For example, each reactive zone of a chemical test strip having multiple reactive zones may have a certain concentration threshold that must be reached in order for any particular reactive zone to change color.

In certain exemplary embodiments, the plurality of post-exposure reactive zones provides information related to the presence or concentration of a plurality of individual chemical species within the liquid medium. For example, two chemical species may typically be present together in a particular liquid medium. A chemical test strip may have two reactive zones, one for each of the two chemical species, so that each reactive zone changes color to indicate the concentration of each chemical species.

In certain exemplary embodiments, a digital image or similar record of the at least one reactive zone is created using the imaging device. In certain exemplary embodiments, the imaging device is a hand held device. In certain exemplary embodiments, the hand held device weighs no more than 1 lb. In certain exemplary embodiments, creation of the digital image is carried out in typical fashion using a digital camera of any type. In certain exemplary embodiments, the digital camera is a hand held digital camera. In certain exemplary embodiments, the digital camera is incorporated into or otherwise operably attached to a mobile device (e.g., a mobile phone, tablet, media player, etc.). In certain exemplary embodiments, the digital camera is incorporated into or otherwise operably attached to a tablet device. In certain exemplary embodiments, the digital camera is incorporated into or otherwise operably attached to a computer. In certain exemplary embodiments, the computer is a desktop computer. In certain exemplary embodiments, the computer is a laptop computer.

In certain exemplary embodiments, the image analyzing software has been incorporated into (e.g., is executed by) the imaging device. In certain exemplary embodiments, the image analyzing software is accessed from a location remote from the imaging device. In certain exemplary embodiments, the image analyzing software may be partially incorporated into the imaging device and partially accessed from a location remote from the imaging device. In certain exemplary embodiments, the image is transmitted via a network, such as a cellular network or the Internet. For some exemplary embodiments, the image analyzing software may include a user interface in the form of an "app" or the like on a mobile device. In certain exemplary embodiments, the app may perform one or more of the following functions:

enable storage of data and/or analysis thereof, upload data and/or analysis thereof to a central server or other specified location, provide "geo-tagging" of data and/or analysis thereof, and recommend a plan of action (as described herein). In certain exemplary embodiments, the app may generate reports that illustrate, describe, and/or summarize the data and/or analysis thereof. In certain exemplary embodiments, the app may perform and report statistical analysis calculations related to the data and/or analysis thereof.

As previously discussed, image analyzing software is used to analyze an image of the at least one reactive zone of the chemical test strip. For example, the image analyzing software could evaluate a value associated with each individual pixel of the image. In certain exemplary embodiments, the image analyzing software automatically analyzes the digital image upon its creation. In other words, once the image is created, the software analyzes the image without any further user input or action. For example, such an exemplary embodiment could be carried out by an "app" or the like installed on or otherwise interfaced with a mobile device, a tablet device, a computer, a digital camera, or any other device employing suitable logic.

In certain exemplary embodiments, the digital image is optionally cropped to isolate a particularly representative section of the digital image of the at least one reactive zone, i.e., a section of the at least one reactive zone that is most likely to indicate the concentration of the chemical species at issue. Cropping may be necessary depending on inconsistent exposure of the at least one reactive zone to the liquid medium or portion thereof, or perhaps for reasons related to the quality of the chemical test strip employed. In certain exemplary embodiments, the cropping is performed "by hand," i.e., by a person using the digital imaging device or another computing device. In certain exemplary embodiments, the cropping is performed automatically by the image analyzing software.

In certain exemplary embodiments, the image analyzing software analyzes at least one colorimetric parameter of the reactive zone of the chemical test strip. For example, the at least one colorimetric parameter may be selected from the group consisting of: tint, color value, color intensity (shade), brightness, contrast, and combinations thereof. Such a measurement allows for a reliable determination of a concentration of at least one chemical species within the liquid medium.

The image analyzing software analyzes at least one colorimetric parameter of the digital image by calculating at least one value associated with the colorimetric parameter, wherein the at least one value corresponds to the concentration of the at least one chemical species present in the liquid medium.

In certain exemplary embodiments, the analysis may be performed by the image analyzing software as follows. When a digital image is created, the imaging device encodes each pixel of the image into a digital file. The digital image can subsequently be displayed on a monitor or screen by accessing the digital file. The code of the digital file can be mathematically manipulated, where such manipulation may provide generally more meaningful information (as opposed to the code) corresponding to any one or more of several colorimetric parameters. For color value, a coordinate system may be used to mathematically describe the color of anything, including a digital image or portion thereof. In certain exemplary embodiments, the coordinate system comprises red, green, and blue values. In certain exemplary embodiments, the analysis calculates a red value, a green value, and a blue value by mathematical manipulation of the code of the image or portion thereof, whereby one or more of these values are used for mathematical determination of the concentration of the at least one chemical species in the liquid medium (and optionally the recommended plan of action). In certain exemplary embodiments, the code of the pixels is analyzed for brightness, with a brightness value calculated according to the analysis (mathematical manipulation) of the code of the image or portion thereof. In certain exemplary embodiments, the combination of color and brightness values is analyzed. In certain exemplary embodiments, the calculated values provide data in standardized units that relates to the at least one colorimetric parameter. For example, a group of calculated color values may form a coordinate in the Lab color space. One of ordinary skill in the art will appreciate that any suitable algorithm for performing the aforementioned image analysis could be used.

For embodiments having multiple zones (reactive zones and/or standard zone and/or exposure zone), images of each zone should be created and compared or contrasted using the image analyzing software. In certain embodiments, the comparing or contrasting involves performing mathematical functions to manipulate the data of the several digital images to provide the information sought by the user. The comparing or contrasting may sum or average data related to one or more digital images depending on the analysis at hand.

The use of a chemical test strip that includes at least one standard zone in addition to the at least one reactive zone allows for active standardization, i.e., colorimetric analysis by digitally contrasting two digital images or two different parts of the same digital image: one of the standard zone and the other of the reactive zone. Active standardization provides a way of digitally (i.e., mathematically) determining the amount of colorimetric change of the reactive zone, and therefore the concentration of a chemical species. In certain exemplary embodiments, the image analyzing software performs active standardization.

In certain exemplary embodiments, the gathered data may indicate that a certain action or group of actions should be taken to maintain or improve the industrial water system. In certain exemplary embodiments, such an action may be merely a recommended plan of action. In certain exemplary embodiments, the user may take action to maintain or improve the industrial water system according to the recommended plan of action, wherein the recommended plan of action involves making operational and/or chemical treatment modifications to the industrial water system. Non-limiting examples of operational actions may include changing a set point related to a controlled, process-related (as opposed to treatment-related) physical parameter (e.g., a temperature set point, a pressure set point, a flow rate set point, etc., which in turn may operate process-related equipment); operating process-related equipment (e.g., changing pump and/or mixer speed, and/or valve position, etc., which expressly includes performing blowdown); re-sourcing makeup water; and combinations thereof. Non-limiting examples of chemical actions may include employing or changing a chemical treatment regimen as further described herein. These recommendations or actions could be determined by analyzing gathered data along with known parameters of the process being analyzed.

In certain exemplary embodiments, the image analyzing software automatically performs or otherwise assists with the additional function of determining, implementing, and/or modifying a chemical treatment regimen for the industrial water system. In certain exemplary embodiments, the image analyzing software inputs at least one value into a second software package that determines a chemical treatment regimen for the industrial water system. Non-limiting examples of modifying a chemical treatment regimen may include changing an injection rate of a treatment chemical, changing a concentration set point of a treatment chemical, changing a treatment chemical, recommending a new treatment chemical, and combinations thereof. In yet further exemplary embodiments, the image analyzing software outputs information so that a user may determine a chemical treatment regimen for the industrial water system.

In certain exemplary embodiments, data may be output or otherwise transmitted to an outputting device. As used herein, the term "data" refers to any raw data, calculated values, images, recommended chemical treatment regimen, or combinations thereof. In certain exemplary embodiments, the data is output to an electronic display, e.g., a monitor or screen of some sort, which includes but is not limited to a display of a hand held or otherwise portable device. In certain exemplary embodiments, the data is output to a data store or similar peripheral device. In certain exemplary embodiments, the data is output into a database for historic or future reference. In certain exemplary embodiments, the data is output to a printer or similar peripheral device.

In certain exemplary embodiments of the disclosed methods, the methods employ at least one light. In certain exemplary embodiments, a first light illuminates the chemical test strip from the rear (i.e., the side not facing the imaging device). In certain exemplary embodiments, the first light is an LED. In certain exemplary embodiments, a second light illuminates the chemical test strip from the front (i.e., the side facing the imaging device). In certain exemplary embodiments, the second light is an LED. In certain exemplary embodiments, the second light is a built-in flash of the imaging device. In certain exemplary embodiments, at least one of the LEDs is a flash LED.

While the exemplary methods disclosed herein may be capable of reliable practice using only a chemical test strip and an imaging device, in certain other exemplary embodiments, the methods further employ a chemical test strip holder to hold the chemical test strip during the imaging of the at least one reactive zone. The chemical test strip holder may address concerns related to reliability and repeatability of the methods. While not wishing to be bound to any theory, reliability and repeatability in practicing the disclosed methods multiple times for multiple images is believed to be optimal when the images are created in a consistently uniform manner at consistently uniform lighting and a consistently uniform distance between the chemical test strip and the imaging device, wherein the reactive zones of multiple chemical test strips are consistently exposed in the same manner. While the chemical test strip holder does not address the consistency in exposure to the liquid medium, it does attempt to address the consistency issues related to imaging.

Referring to the figures, FIG. 1 illustrates an exemplary embodiment of an imaging device imaging a reactive zone of a chemical test strip, which may be a post-exposure reactive zone. The exemplary embodiment illustrated in FIG. 1 is directed to a system for colorimetrically determining a concentration of at least one chemical species in a liquid medium. A chemical test strip 300 having a reactive zone 310 has already been exposed to a liquid medium (not shown). The reactive zone 310 is imaged by an imaging device 10, which comprises an actuator 11, a lens 12, and optionally a built-in flash 13. Operably connected to the imaging device 10 is image analyzing software 20. The image analyzing software 20 is shown in FIG. 1 as connected to the imaging device 10 with a dotted line. The dotted line is used to denote that the imaging device 10 and the image analyzing software may be connected or otherwise interfaced in any suitable manner. For example, the image analyzing software 20 may be embedded in logic of the imaging device 10. As another example, the image analyzing software 20 may be remotely located at another processing unit (not shown). As yet another example, the image analyzing software 20 may be partially located on the imaging device 10 and partially on a remote processing unit (not shown). While the imaging device 10 of FIG. 1 appears to take the form of a hand held camera, it is important to note that, as discussed herein, the imaging device 10 can be any device capable of creating a digital image that is suitable for colorimetric analysis.

Figure 2:
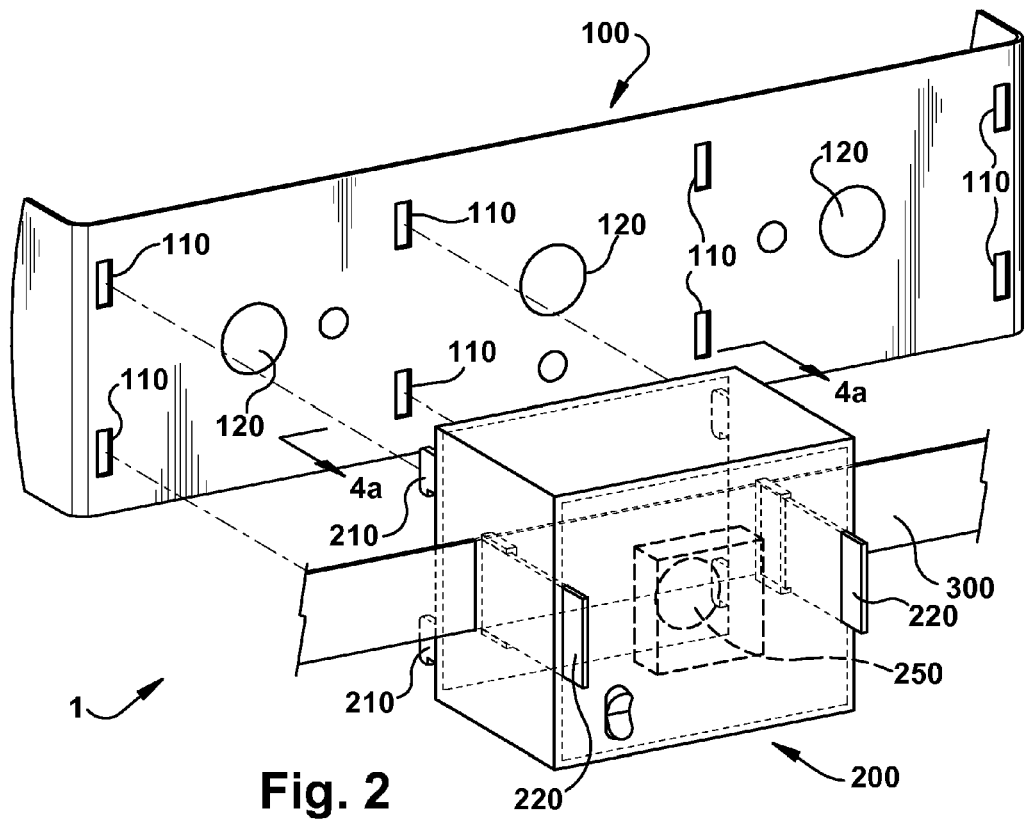
FIG. 2 illustrates an exemplary embodiment of a chemical test strip holder that may be utilized to practice certain embodiments of the disclosed methods and systems.

FIG. 2 illustrates an exemplary embodiment of a chemical test strip holder 1. The chemical test strip holder 1 creates an imaging chamber 240 (FIG. 4a) that provides uniformity in lighting and distance between the imaging device 10 (FIG. 1) and the chemical test strip 300 during imaging of the reactive zone 310 (FIG. 1). While a two-piece embodiment is illustrated, those of skill in the art will readily recognize that, if a single imaging device, or multiple imaging devices having the same lens-flash configuration, are to be used in repeatedly practicing the methods, the chemical test strip holder 1 may need only one piece that performs the function of the illustrated embodiment. Another exemplary embodiment of a chemical test strip holder 1 may have one large opening for both the lens and the flash, wherein the large opening could be closed with the imaging device itself so as to control the lighting within the imaging chamber 240. Furthermore, in certain exemplary embodiments, the chemical test strip holder 1 may be constructed of more than two pieces. Such embodiments are contemplated by the general inventive concepts.

In certain exemplary embodiments, the chemical test strip holder 1 comprises at least two distinct pieces that are capable of removably attaching to one another. In certain exemplary embodiments, a first piece of the chemical test strip holder 1 is an imaging device adaptor 100 that can accommodate several different types of imaging devices that may have lenses in varying locations. In those exemplary embodiments employing the chemical test strip holder 1, the chemical test strip holder 1 may comprise a series of circular holes 120 that allow for potential camera and LED locations. In certain exemplary embodiments, the imaging device adaptor 100 is additionally capable of being operably attached to a second piece as further described herein. In certain exemplary embodiments, the imaging device adaptor 100 comprises rectangular slots 110 for mounting a test strip stabilizer 200, as the second piece of the chemical test strip holder 1, so as to create an enclosure that allows for more uniform imaging of the reactive zone of the chemical test strip 300, and therefore greater repeatability across multiple images and chemical test strips.

Figure 3:
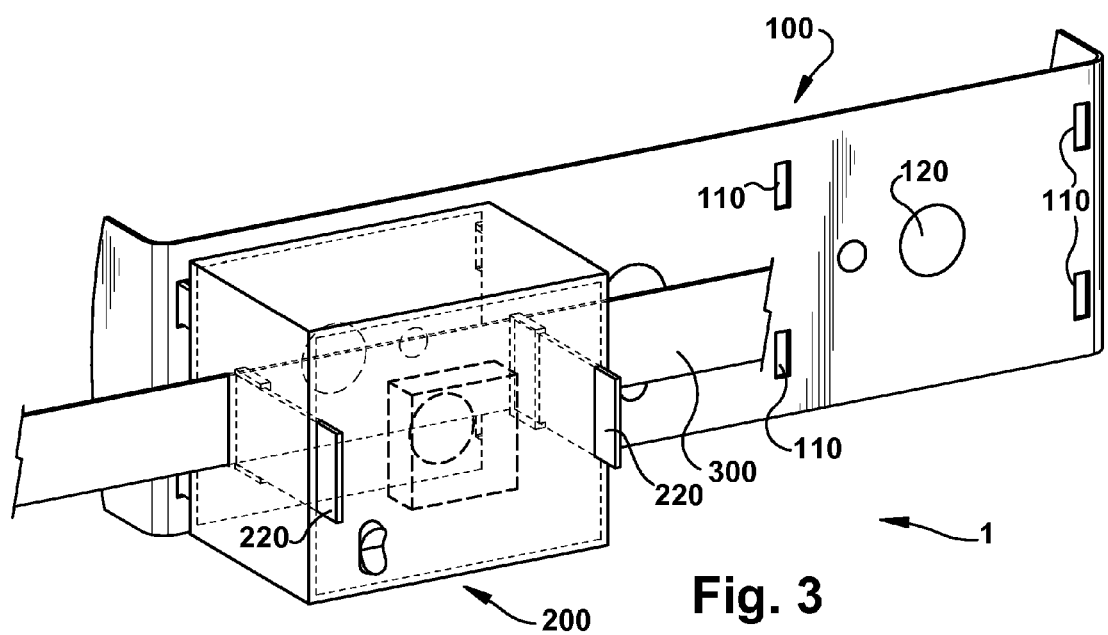
FIG. 3 illustrates the exemplary embodiment of FIG. 2 when assembled.

Turning to FIG. 3, FIG. 3 illustrates the imaging device adaptor 100 and the test strip stabilizer 200 attached to each other at a position on the imaging device adaptor 100 for the two-piece embodiment illustrated in FIG. 2.

Figure 4A:
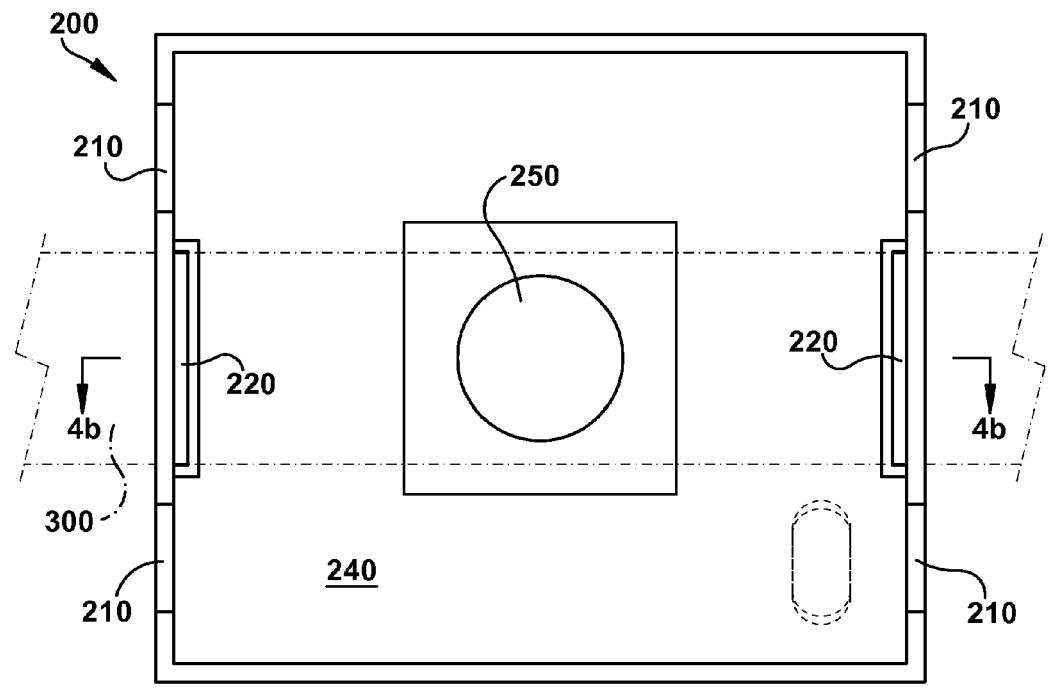
FIG. 4a shows a facing view of the inside of the exemplary embodiment of the test strip stabilizer illustrated in FIGS. 2 and 3.
Figure 4B:
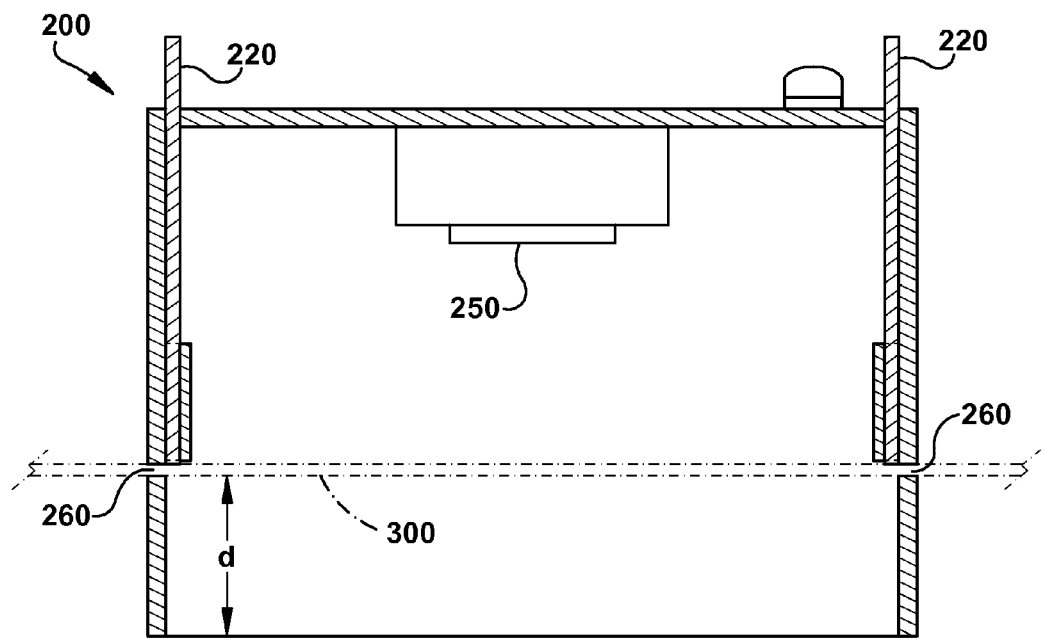

FIGS. 4a and 4b further illustrate the test strip stabilizer 200. In certain exemplary embodiments, the test strip stabilizer 200 is a box-shaped device that forms an imaging chamber 240 and has one side essentially open. The essentially open side is covered by the imaging device adaptor 100 when the two pieces are attached to one another. In certain exemplary embodiments, the test strip stabilizer 200 may comprise rectangular extensions 210 that interface with the rectangular slots 110 of the imaging device adaptor 100 when present.

In certain exemplary embodiments, the test strip stabilizer 200 comprises at least one test strip display slot 260. In certain exemplary embodiments, each test strip display slot 260 is opened and closed via a door 220. In certain exemplary embodiments, the door 220 is a sliding panel. The distance "d" indicates the distance between the imaging device adaptor 100 and the chemical test strip 300. Uniformity in the distance "d" and the lighting during imaging is believed to provide improved reliability and repeatability in the inventive methods and systems.

In certain exemplary embodiments, a rear side of the test strip stabilizer 200 includes a hole that allows for the aforementioned rear illumination via the first light, or the rear side may include a solid wall with a built-in light source, either of which can be illustrated as item 250 of FIG. 4a (note: Item 250 in FIG. 4b illustrates the built-in light source option). In certain exemplary embodiments, the built-in light source, when employed, is a built-in LED. In other words, the built-in LED, when present, would be the first light. Such a built-in LED may be battery-powered and may also include an on-off switch.

Any patents referred to herein, are hereby incorporated herein by reference, whether or not specifically done so within the text of this disclosure.

To the extent that the terms "include," "includes," or "including" are used in the specification or the claims, they are intended to be inclusive in a manner similar to the term "comprising" as that term is interpreted when employed as a transitional word in a claim. Furthermore, to the extent that the term "or" is employed (e.g., A or B), it is intended to mean "A or B or both A and B." When the applicants intend to indicate "only A or B but not both," then the term "only A or B but not both" will be employed. Thus, use of the term "or" herein is the inclusive, and not the exclusive use. See Bryan A. Garner, A Dictionary of Modern Legal Usage 624 (2d ed. 1995). Also, to the extent that the terms "in" or "into" are used in the specification or the claims, it is intended to additionally mean "on" or "onto." Furthermore, to the extent that the term "connect" is used in the specification or the claims, it is intended to mean not only "directly connected to," but also "indirectly connected to" such as connected through another component or components. In the present disclosure, the words "a" or "an" are to be taken to include both the singular and the plural. Conversely, any reference to plural items shall, where appropriate, include the singular.

All ranges and parameters disclosed herein are understood to encompass any and all sub-ranges assumed and subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more (e.g., 1 to 6.1), and ending with a maximum value of 10 or less (e.g., 2.3 to 9.4, 3 to 8, 4 to 7), and finally to each number 1, 2, 3, 4, 5, 6, 7, 8, 9, and 10 contained within the range.

The general inventive concepts have been illustrated, at least in part, by describing various exemplary embodiments thereof. While these exemplary embodiments have been described in considerable detail, it is not the Applicant's intent to restrict or in any way limit the scope of the appended claims to such detail. Furthermore, the various inventive concepts may be utilized in combination with one another (e.g., one or more of the first, second, third, fourth, etc., exemplary embodiments may be utilized in combination with each other). Additionally, any particular element recited as relating to a particularly disclosed embodiment should be interpreted as available for use with all disclosed embodiments, unless incorporation of the particular element would be contradictory to the express terms of the embodiment. Additional advantages and modifications will be readily apparent to those skilled in the art. Therefore, the disclosure, in its broader aspects, is not limited to the specific details presented therein, the representative apparatus, or the illustrative examples shown and described. Accordingly, departures may be made from such details without departing from the spirit or scope of the general inventive concepts.

The invention claimed is:

1. A method of determining concentration of a chemical species in industrial cooling water, the method comprising:
    exposing a reactive zone of a chemical test strip to industrial cooling water thereby creating a post-exposure reactive zone;
    imaging the post-exposure reactive zone using an imaging device thereby creating a digital image of the post-exposure reactive zone;
    optionally cropping the digital image of the post-exposure reactive zone to isolate a portion of the digital image for analysis;
    analyzing a colorimetric parameter of at least the portion of the digital image of the post-exposure reactive zone using image analyzing software to determine the concentration of the chemical species; and
    optionally outputting the determined concentration of the chemical species of the industrial cooling water.

2. The method of claim 1, further comprising illuminating the chemical test strip from the rear during the imaging of the post-exposure reactive zone.

3. The method of claim 1, further comprising taking action based on the determined concentration.

4. The method of claim 3, wherein the action taken is modification of a chemical treatment regimen, the modification selected from changing an injection rate of a treatment chemical, implementing chemical treatment, and combinations thereof.

5. The method of claim 4, further comprising illuminating the chemical test strip from the rear during the imaging of the post-exposure reactive zone.

6. The method of claim 4, wherein the modification is changing an injection rate of a treatment chemical.

7. The method of claim 6, further comprising illuminating the chemical test strip from the rear during the imaging of the post-exposure reactive zone.

8. The method of claim 3, wherein the action taken is an operational action selected from changing a set point related to a controlled, process-related physical parameter, operating process-related equipment, re-sourcing makeup water, and combinations thereof.

9. The method of claim 8, further comprising illuminating the chemical test strip from the rear during the imaging of the post-exposure reactive zone.

10. The method of claim 1, further comprising automatically recommending a plan of action to maintain efficient operation of an industrial cooling water system based on the analysis of the digital image of the post-exposure reactive zone.

11. The method of claim 10, wherein the plan of action includes at least one of implementation and modification of a chemical treatment regimen.

12. The method of claim 1, wherein the concentration of the chemical species is determined via a color change of the post-exposure reactive zone.

13. The method of claim 1, wherein the concentration of the chemical species is determined via a plurality of post-exposure reactive zones on the chemical test strip.

14. The method of claim 1, wherein the colorimetric parameter is selected from tint, color value, color intensity, brightness, contrast, and combinations thereof.

15. The method of claim 1, further comprising using a chemical test strip holder to hold the chemical test strip during the imaging of the post-exposure reactive zone.

16. The method of claim 1, wherein the chemical species is selected from calcium, magnesium, total hardness, acidity, chloride, sulfate, ortho-phosphate, alkalinity, p-alkalinity, corrosion inhibitor, dispersant polymer, biocide, and combinations thereof.

17. The method of claim 16, further comprising illuminating the chemical test strip from the rear during the imaging of the post-exposure reactive zone.

18. The method of claim 1, wherein the chemical species is selected from calcium, magnesium, total hardness, acidity, chloride, sulfate, and combinations thereof.

19. The method of claim 1, wherein the chemical species is a corrosion inhibitor.

20. The method of claim 19, wherein the corrosion inhibitor is an aromatic azole.

\* \* \* \* \*

UNITED STATES PATENT AND TRADEMARK OFFICE
CERTIFICATE OF CORRECTION

PATENT NO. : 9,841,382 B2  
APPLICATION NO. : 15/142605  
DATED : December 12, 2017  
INVENTOR(S) : Walicki Page 1 of 1

It is certified that error appears in the above-identified patent and that said Letters Patent is hereby corrected as shown below:

In the Claims

Column 13, Line 15, please delete "ortho-phosphate, alkalinity, p-alkalinity" and add --ortho-phosphate, m-alkalinity, p-alkalinity--

Signed and Sealed this  
Sixth Day of March, 2018

Andrei Iancu  
*Director of the United States Patent and Trademark Office*